United States Patent [19]

Tsukada et al.

[11] Patent Number: 5,840,705
[45] Date of Patent: Nov. 24, 1998

[54] α-GLUCOSIDASE INHIBITOR, COMPOSITION PRINCIPALLY COMPRISING SUGAR AND CONTAINING THE SAME, SWEETENER, FOOD AND FEED

[75] Inventors: Masayuki Tsukada; Hiroyuki Takeda; Norio Maeda; Yasunori Fukumori; Norio Shiomi; Shuichi Onodera, all of Hokkaido; Takuji Fujisawa, Fukuoka, all of Japan

[73] Assignee: The Hokuren Federation of Agricultural Cooperatives, Japan

[21] Appl. No.: 604,563

[22] Filed: Feb. 21, 1996

[30] Foreign Application Priority Data

Apr. 20, 1995 [JP] Japan ................................. 7-119163

[51] Int. Cl.$^6$ ............................. A01N 43/04; A61K 31/70
[52] U.S. Cl. .................................. 514/43; 435/183; 435/4
[58] Field of Search ................................. 514/42, 43, 62; 435/4, 183; 536/22.1, 25.6, 26.1, 27.1, 27.6

[56] References Cited

U.S. PATENT DOCUMENTS

| | | | |
|---|---|---|---|
| 4,176,201 | 11/1979 | Cook | 426/548 |
| 4,827,036 | 5/1989 | Kameda et al. | 564/462 |

FOREIGN PATENT DOCUMENTS

| | | |
|---|---|---|
| 52-122342 | 10/1977 | Japan . |
| 57-59813 | 9/1980 | Japan . |
| 57-200335 | 6/1981 | Japan . |
| 61-5023 | 6/1984 | Japan . |
| 63-208532 | 2/1987 | Japan . |
| 665080 | 12/1992 | Japan . |

OTHER PUBLICATIONS

Dok et al, 1993, The Harper Collins Illustrated Medical Dictionary, pp. 340 & 420–421.

Wong et al, J. Org. Chem., 1995, vol. 60, No. 6, pp. 1492–1501, "Syumthesis and Evaluation of Homo aza Sugars as Glycosidase Inhibitors".

Tattersall, Diabetic Medicine, 1993; 10, pp. 688–693.

Sonoda et al, Biochimica et Biophysica Acta, 1978, pp. 55–66.

Matsuo et al, Am. J. Clin. Nutr. 1992; 55:3145–75.

Berger Am J Clin Nutr; 1992; 55:318S–95.

Hotta et al, Diabetic Medicine, 1993; 10: 134–138.

Dietary Fiber, 1982, pp. 271–286.

Dietary Fiber Can Prevent Modern Diseases; 1983, pp. 125–137.

*Primary Examiner*—Gary E. Hollinden
*Assistant Examiner*—Dameron Jones
*Attorney, Agent, or Firm*—Lorusso & Loud

[57] ABSTRACT

This invention relates an α-glucosidase inhibitor mildly inhibiting α-glucosidase locally present in the micro-villus of small intestine, a composition principally comprising sugar and containing the inhibitor, a food, a sweetener and a feed. The inhibitor delays the digestion of starch, starch-derived oligosaccharides and sucrose, so that the inhibitor has an action of suppressing rapid increase in blood glucose level and an action of suppressing insulin secretion at a lower level. Thus, the inhibitor is useful for the prophylaxis of obesity and diabetes mellitus. The α-glucosidase inhibitor of the present invention is composed of nucleotide, nucleoside, or base as the structural component of nucleic acid and one or two or more digestible sugars selected from sucrose, starch and starch-derived oligosaccharide. The α-glucosidase inhibitor mildly inhibits the action of α-glucosidase as a digestive enzyme in small intestine, and has effects of suppressing rapid increase in blood glucose level and suppressing insulin secretion at a lower level. In combination with digestible sugars, the α-glucosidase inhibitor is applicable as foods, sweeteners and feeds.

16 Claims, 8 Drawing Sheets

S : Sucrose
A : Adenosine

FIG. 11

S : Sucrose
A : Adenosine

α-GLUCOSIDASE INHIBITOR, COMPOSITION PRINCIPALLY COMPRISING SUGAR AND CONTAINING THE SAME, SWEETENER, FOOD AND FEED

BACKGROUND OF THE INVENTION

1. Technical Field

The present invention relates to an α-glucosidase inhibitor having an action of gradually inhibiting α-glucosidase thereby delaying the digestion of starch, starch-derived oligosaccharides and sucrose, so that the inhibitor suppresses rapid increase in blood glucose level and also suppresses insulin secretion at a lower level; the present invention also relates to a composition principally comprising sugar and containing the same, a sweetener, a food and a feed.

2. Prior Art

It has been reported conventionally that the dietary intake of a higher level of starch with a higher content of vegetable fiber slows down nutritious absorption through small intestine to suppress the elevation of blood glucose level after meals thereby suppressing insulin secretion at a lower level, which is a preventive measure against adult diseases such as obesity and diabetes mellitus [see Dr. Denis Burkitt, "Don't forget fibre in your diet," (Japanese translation; "Dietary fiber can prevent modern diseases," pp. 125–137, issued by Chuo Koron-sha, May 25, 1983); "Dietary fiber," pp. 271–286, issued by Dai-ichi Shuppan Kabushiki Kaisha, May 15, 1982]. Unlike sugars which can freely be added and mixed into a wide variety of foods, however, the application of the dietary fiber to various foods is limited. For example, the dietary fiber of itself is not sweet enough to be used as a sweetener or a sweetening material for use in drinks such as coffee and juice, and cakes and sweets.

In recent years, it has been known that the dosing of α-glucosidase inhibitors inhibits α-glucosidase located in the micro-villus of small intestine, to suppress rapid elevation of blood glucose level after meals and rapid increase in insulin level following the elevation (for example, see Japanese Patent Laid-open No. Sho 52-122342 (1977); Diabetic Medicine, 1993, 10, 688–693, 134–138; Am. J. Clin. Nutr., 1992, 55, 318S–319S; Japanese Patent Laid-open No. Sho 57-200335 (1982); Am. J. Clin. Nutr., 1992, 55, 314S–317S;, and Japanese Patent Laid-Open No. Sho 57-59813 (1982)). Among such α-glucosidase inhibitors, acarbose has been applied as an oral therapeutic agent of diabetes mellitus for insulin-non-dependent diabetes mellitus (abbreviated as "NIDDM"). However, these substances are essentially xenobiotic with safety concerns, so the doses thereof have been regulated strictly.

Furthermore, hardly digestible or slightly digestible oligosaccharides such as fructo-oligosaccharide and galacto-oligosaccharide, or starch hydrolysates and sugar alcohols of other oligosaccharides (for example, maltitol, sugar alcohol of malto-oligosaccharide, sugar alcohols of iso-maltose and its oligosaccharide, reduction-type paratinose, and lactitol), have been used conventionally as sweeteners with lower elevation of blood glucose level because they themselves are hardly digestible or slightly digestible. However, these hardly digestible or slightly digestible oligosaccharides conventionally put to use as sweeteners with lower elevation of blood glucose level have a drawback that the miss dosing thereof may readily cause diarrhea.

Japanese Patent Laid-open No. Sho 61-5023 (1986) and Sho 63-208532 (1988) propose a food and drink which is intended for the suppression of blood glucose level elevation and which is from the raw material gimnemasilvesta from India, having an action of suppressing sugar absorption. The action of the extracts of these gimnemasilvesta and gimnemainodrum is derived from the suppression of sugar absorption. When the extracts are taken at an inappropriate dose, they cause side effects such as too much decrease of blood glucose level and the occurrence of disorders such as diarrhea because sugars not absorbed may reach the large intestine.

Still furthermore, Japanese Patent Laid-Open No. Hei 6-65080 (1994) describes that sugars principally comprising naturally occurring L-arabinose are applicable as a safe α-glucosidase inhibitor. Because arabinose and the like are pentose, however, their browning via heating is unavoidable, so serious limitation is imposed to their mixing and application into foods containing carbohydrate.

As has been described above, because conventional α-glucosidase inhibitors have various disadvantages, the development of an α-glucosidase inhibitor highly safe and beneficial for humans has been expected, provided that the inhibitor is a substance contained in foods of routine intake, having excellent processability, being absorbed through gastro-intestinal tract and effectively usable in bodies.

In accordance with the present invention, thus, investigations have been made on a substance capable of inhibiting α-glucosidase locally present in the micro-villus of small intestine, to provide an α-glucosidase inhibitor which is applicable as a food material, a sweetener and a feed to prevent adult diseases such as obesity and diabetes mellitus and which is suitable for patients with such diseases. In accordance with the present invention, there is provided a composition principally comprising sugar and further containing the α-glucosidase inhibitor, a sweetener, a food and a feed.

DISCLOSURE OF THE INVENTION

Focusing their attention to nucleic acid-related substances as vital essence and being responsible for the transmission and expression of genetic information, and also being known as food materials, the present inventors have examined as to whether or not a wide variety of nucleic acid-related substances have such α-glucosidase inhibiting action. Consequently, the inventors have found that only a specific nucleic acid-related substance has a mild action of inhibiting α-glucosidase. Additionally, the inventors have found that the dosing of the nucleic acid-related substance with such inhibiting action in combination with edible carbohydrate and sugars can suppress rapid increase in blood glucose level immediately after the intake and can also suppress insulin secretion at a lower level. Based on these findings, the following invention has been achieved.

The α-glucosidase inhibitor of the present invention contains one or two or more substances selected from nucleotide, nucleoside, and nucleic acid-derived base as the effective ingredients and characteristically, the inhibitor has a mild inhibitory action of α-glucosidase.

In accordance with the present invention, the term "mild inhibitory action" means an action of the α-glucosidase inhibitor to moderately inhibit the action of a digestive enzyme present in small intestine, i.e., α-glucosidase, provided that the inhibitor is blended within a range of 0.5 to 30 wt.parts to the total carbohydrate (total sugar materials) 100 wt.parts in the case of the intake of the α-glucosidase inhibitor together with carbohydrate. Because the appropriate dose of the α-glucosidase inhibitor of the present invention is far higher than the individual doses of conventional α-glucosidase inhibitors, it can be said that the α-glucosidase inhibitor of the present invention has such "mild inhibitory action."

In accordance with the present invention, the nucleotide as the effective ingredient of the α-glucosidase inhibitor includes adenylic acid, guanylic acid, cytidylic acid, uridylic acid, inosinic acid, or the salts thereof. Nucleotide can be generated through enzymatic hydrolysis of nucleic acid with enzymes such as nuclease. Additionally, nucleotide is present as a flavor component in Cortinellus shiitake and asparagus.

In accordance with the present invention, the nucleoside as the effective ingredient of the α-glucosidase inhibitor includes guanosine, deoxyguanosine, adenosine, deoxyadenosine, cytidine, uridine, inosine or deoxyinosine.

In accordance with the present invention, the base of the structural component of nucleic acid as the effective ingredient of the α-glucosidase inhibitor includes cytosine- and adenine hydrochloride salts.

As the essential effective ingredients, the α-glucosidase inhibitor of the present invention should contain the nucleotide, the nucleoside and/or the base of the structural component of nucleic acids. Concurrently, the α-glucosidase inhibitor may contain nucleic acid-related substances and nucleic acid degradation products at various degradation stages, other than the ingredients.

The composition principally comprising sugar and having an action of digesting sugar mildly and an action of suppressing insulin secretion at a lower level contains as the essential components the α-glucosidase inhibitor and one or two or more digestible sugars selected from sucrose, starch and starch-derived oligosaccharides. In the composition principally comprising sugar in accordance with the present invention, the α-glucosidase inhibitor should be blended to a final concentration of 0.5 to 30 wt. % into the composition principally comprising sugar. If the α-glucosidase inhibitor is below 0.5 wt. % in the composition principally comprising sugar, the action of inhibitingα-glucosidase is so unsatisfactory that the effect of suppressing rapid increase in blood glucose level or the effect of suppressing insulin secretion at a lower level is not exerted. If the α-glucosidase inhibitor of the present invention is above 30 wt. % in the composition principally comprising sugar, the taste specific to nucleic acid is likely to be too strong (for example, the generation of bad taste due to too much flavor of nucleic acid-series seasonings).

For more detailed description of specific examples of the α-glucosidase inhibitor, the α-glucosidase inhibitor containing as the effective ingredient adenosine, guanosine, inosine, cytosine, adenylic acid Na, guanylic acid Na, inosinic acid or the like should be blended preferably to a final concentration of 0.5 to 30 wt. % of the composition principally comprising sugar; the α-glucosidase inhibitor containing as the effective ingredient deoxyadenosine, deoxyinosine, deoxyguanosine, uridine, or cytidine, should be blended preferably to a final concentration of 10 to 30 wt. % to the composition principally comprising sugar.

Toxicity Test of Single Oral Dose

Crj:CD (SD) rats of age 6 weeks were grouped into each group of 5 male and 5 females. At a single oral dose of adenosine or inosine at 2.5 g/kg or 5.0 g/kg, 5 groups in total (2 adenosine groups, 2 inosine groups plus a control group) were prepared. Two weeks in the course, no animal death was observed; no specific change in the general status, weight change and organ findings was observed. Based on these outcome, the minimum lethal doses of adenosine and inosine are estimated above 5 g/kg, which indicates that both the substances are at low toxicity.

By preparing the α-glucosidase inhibitor of the present invention into a composition principally comprising sugar in combination with one or two or more digestible sugars selected from sucrose, starch and starch-derived oligosaccharide, the composition exerts mild digestion of sugar and suppresses insulin secretion at a lower level after the intake in human subjects or in animals.

The composition principally comprising sugar, in combination with the α-glucosidase inhibitor of the present invention and one or two or more digestible sugars selected from sucrose, starch and starch-derived oligosaccharide, is applicable as a sweetener, which exerts mild digestive action of sugar and suppresses insulin secretion at a lower level after the indigestion in humans or in animals.

When the α-glucosidase inhibitor of the present invention is directly added into foods principally comprising carbohydrate for use, which are then ingested into humans and animals, the mild sugar digestive action of the foods can be exerted, together with the suppression of insulin secretion at a low level. Examples of such foods principally comprising carbohydrate include pasta, noodle, bread, cookies, cakes, chocolate, candy, chewing gum, various sweets, a variety of soft drinks such as juice and cola and the like.

When the α-glucosidase inhibitor of the present invention is used in a food with an essentially lower carbohydrate content or slightly containing carbohydrate, for example, coffee, tea, or a variety of teas, the inhibitor may be used in the form of a composition or a sweetener, comprising sugar composed of one or two or more digestible sugars selected from sucrose, starch and starch-derived oligosaccharide, in combination with α-glucosidase inhibitor.

The foods with addition of the α-glucosidase inhibitor of the present invention may be prepared into healthy foods, foods for diabetic patients, and foods for slimming bodies (for diet). Furthermore, the α-glucosidase inhibitor of the present invention can be added to feeds, which are applicable to the dietary feeds and to the prophylaxis of diabetic mellitus for livestock and pets.

In the sweetener, food and feed in accordance with the present invention, preferably, the α-glucosidase inhibitor may be blended to a final concentration of 0.5 to 30 wt.parts to the total sugar materials 100 wt.parts.

BEST MODE FOR CARRYING OUT THE INVENTION

The present invention will now be explained in detail in examples.

EXAMPLE 1

The present Example 1 is an example of inosine inhibition of the porcine intestinal digestive enzyme α-glucosidase.

As substrates, 20 mM sucrose (Suc) and 2% soluble starch (S-Starch) were prepared in solution. 0.5 ml each of these solutions was placed in a test tube, into which was added a 20 mM inosine solution (0 to 0.4 ml) diluted with 0.1M potassium phosphate buffer, pH 7.0, followed by addition of 0.1M potassium phosphate buffer, pH 7.0 (0.4 to 0 ml). In other words, the buffer solution was added at such a volume that the total volume of the inosine solution and the buffer should be 0.4 ml finally. To the mixture was added a crude enzyme solution from porcine intestine (2-fold dilution; 0.1 ml) for reaction at 37° C. for 30 minutes. Subsequently, 2M Tris-HCl buffer, pH 7.0 (2 ml) was added to terminate the reaction. The level of glucose generated via the enzyme reaction was assayed by an enzyme method via glucose oxidase.

The enzyme solution prepared as follows was used as the enzyme solution for the enzyme inhibition. More specifically, the inner wall of tunica mucosa intestini tenuis was resected from a pig immediately after the pig was sacrificed to death, which was then homogenized in 0.1M potassium phosphate buffer, pH 7.0 containing 5 mM EDTA, prior to centrifuging to recover the precipitate. The precipitate was suspended in a small amount of the same buffer, to which was then added 5-fold volume of the buffer additionally containing 1% Triton X-100, for stirring at 0° C. for 60 minutes to extract the enzyme. After centrifuging to remove the precipitate, the extracts were dialyzed in 0.01M potassium phosphate buffer, pH 7.0, to recover the crude enzyme solution.

Figure 1:
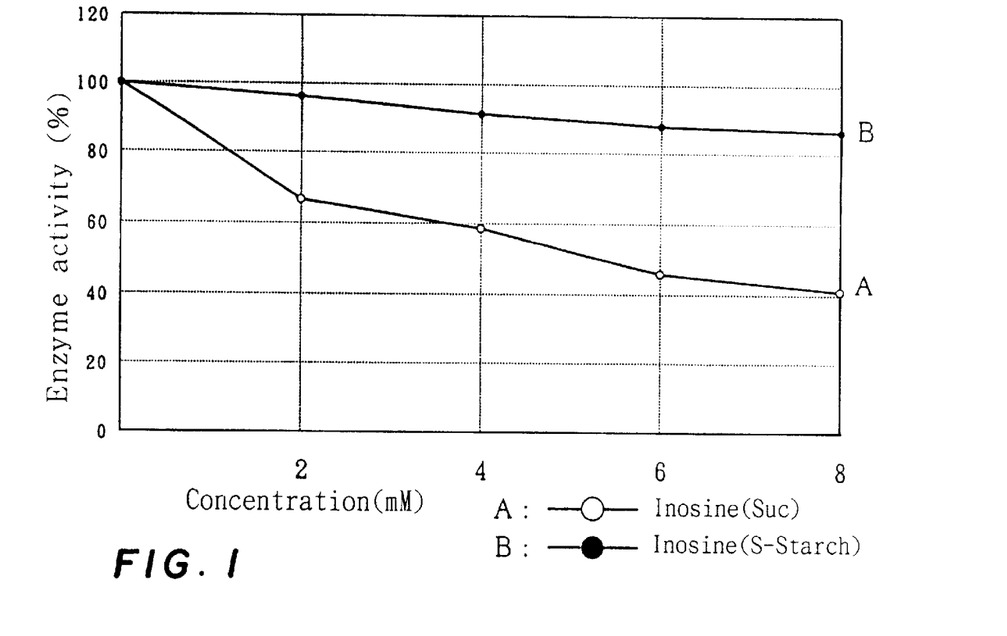
FIG. 1 depicts a graph of the inosine action of inhibiting a porcine intestinal digestive enzyme, α-glucosidase.

The results are shown in the graph of FIG. 1. In the graph of FIG. 1, the inosine level in the reaction solution is represented on the axis of abscissa; the enzyme activity is represented on the axis of ordinate. The enzyme activity in the reaction of the enzyme with substrates alone, is defined and represented as 100%. As shown in FIG. 1, inosine consequently decreased the enzyme activity as the inosine level was elevated (at the maximum concentration of 8 mM/liter) in the presence of the substrates, i.e., sucrose (Suc) and soluble starch (S-Starch). In conclusion, it is indicated that inosine inhibits the action of the digestive enzyme α-glucosidase (maltase, sucrase, etc.).

EXAMPLE 2

The present Example 2 is an example of nucleoside (adenosine, guanosine, cytidine and uridine) for the inhibition of the porcine intestinal digestive enzyme α-glucosidase.

Figure 2:
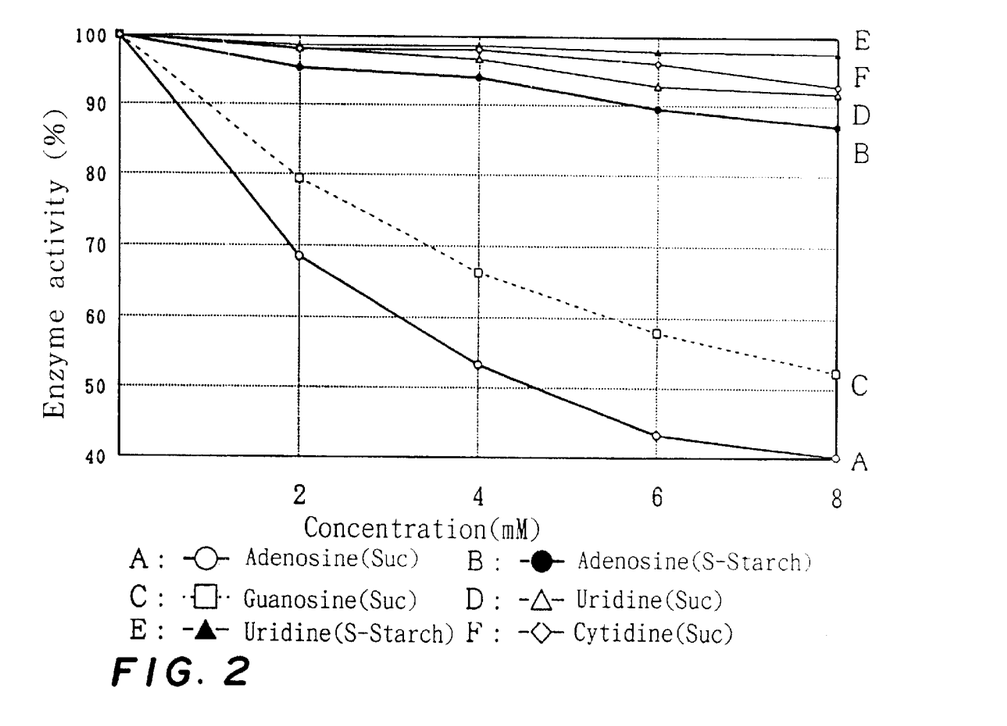
FIG. 2 depicts a graph of the actions of adenosine, guanosine, uridine and cytidine for inhibiting a porcine intestinal digestive enzyme, α-glucosidase.

Using the same substrates and α-glucosidase as in Example 1, the test of nucleosides (adenosine, guanosine, cytidine and uridine) as the RNA (ribonucleic acid) structural components for the inhibition of intestinal enzymes, was carried out by the same method as in Example 1. The results are shown in FIG. 2. In FIG. 2, consequently, it is indicated that the nucleosides decrease the enzyme activity as the elevation of the nucleoside level (at the maximum concentration of 8 mM/liter) when the substrates were sucrose (Suc) and soluble starch (S-Starch). In other words, the nucleosides having purine bases (adenosine and guanosine) strongly inhibit the digestive enzyme α-glucosidase (maltase, sucrase and the like). Furthermore, it is indicated that the nucleosides having pyrimidine bases (cytidine and uridine) inhibit the action of the digestive enzyme α-glucosidase more weakly than those nucleosides having the purine bases.

EXAMPLE 3

The present Example 3 is an example of the pyrimidine base (cytosine) and purine base (adenine hydrochloride salt) to inhibit the porcine intestinal digestive enzyme α-glucosidase.

Using the same substrates and α-glucosidase as in the Example 1, the purine base (adenine hydrochloride salt) was neutralized with a KOH solution. Then, the test of the individual bases for the inhibition of the intestinal enzyme was carried out by the same method as in the Example 1.

Figure 3:
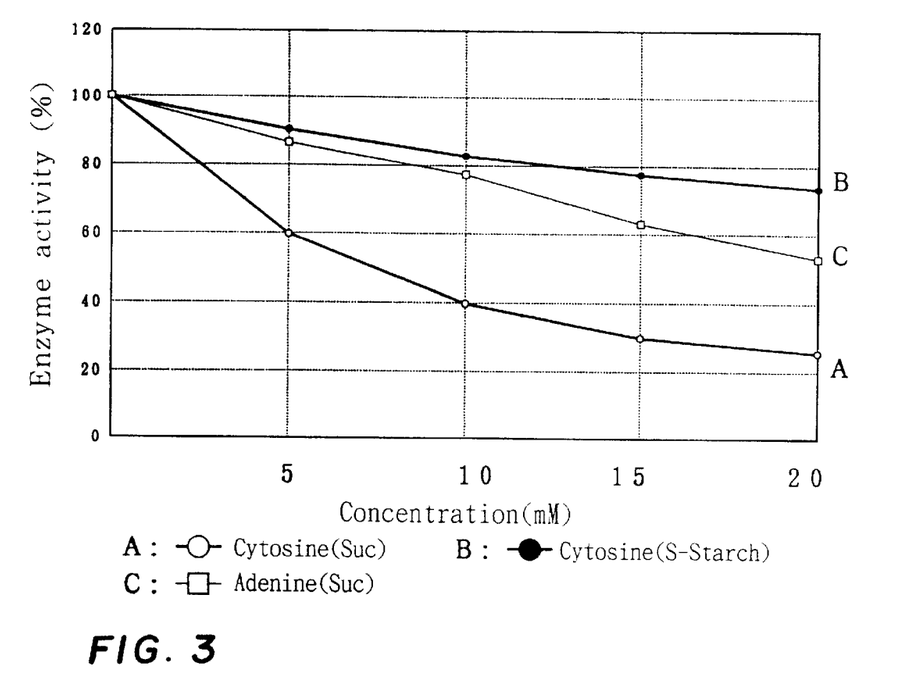
FIG. 3 depicts a graph of the actions of cytosine and adenine for inhibiting a porcine intestinal digestive enzyme, α-glucosidase.

The results are shown in FIG. 3. In FIG. 3, consequently, the enzymatic activity is decreased as the increase of the pyrimidine base (cytosine) (at the maximum concentration of 20 mM/liter) when the substrates are sucrose (Suc) and soluble starch (S-Starch), while the purine base (adenine hydrochloride salt) consequently decreases the enzyme activity in a similar fashion when the substrate is sucrose. In other words, it is indicated that the bases of nucleic acids inhibit the action of the digestive enzyme α-glucosidase.

EXAMPLE 4

The present Example 4 is an example of nucleoside (deoxyadenosine and deoxyguanosine) to inhibit the porcine intestinal digestive enzyme α-glucosidase.

Figure 4:
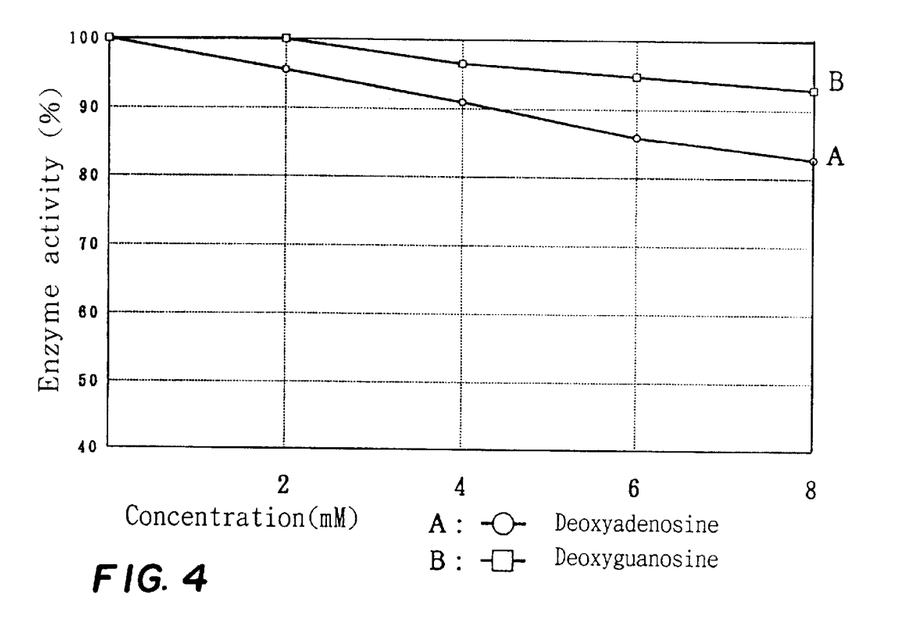
FIG. 4 depicts a graph of the actions of deoxyadenine and deoxyguanosine for inhibiting a porcine intestinal digestive enzyme, α-glucosidase.

Using the same substrates and α-glucosidase as in the Example 1, the test of the nucleosides (deoxyadenosine and deoxyguanosine) as DNA (deoxyribonucleic acid) structural components for inhibiting the intestinal enzyme was carried out by the same method as in the Example 1. The results are shown in FIG. 4. In FIG. 4, consequently, the nucleosides decrease the enzyme activity as the increase of the nucleoside levels (at the maximum concentration of 8 mM/liter) when the substrate is sucrose (Suc). In other words, the nucleosides (deoxyadenosine and deoxyguanosine) as the DNA structural components inhibit the digestive enzyme α-glucosidase.

COMPARATIVE EXAMPLE 1

In Comparative Example 1, examination has been made of the action of nucleosides (thymidine and deoxycytidine) on the porcine intestinal digestive enzyme α-glucosidase.

Using the same substrates and α-glucosidase as in the Example 1, experimental investigation has been made as to whether or not the nucleosides (thymidine and deoxycytidine) as DNA (deoxyribonucleic acid) structural components have an action of inhibiting the intestinal enzyme, by the same method as in the Example 1. The results are shown in Table 1. The enzyme activity is defined as 100% with no addition of any of the nucleosides, and specific activity (%) to the activity is shown at individual levels of each of the nucleosides.

TABLE 1

| Name of substance | Specific activity to additive concentration | | | | |
|---|---|---|---|---|---|
| | 0 mMol/l | 2 mMol/l | 4 mMol/l | 6 mMol/l | 8 mMol/l |
| Deoxycytidine | 100.0 | 101.3 | 98.0 | 99.3 | 102.2 |
| Thymidine | 100.0 | 98.2 | 98.9 | 94.5 | 97.6 |

In Table 1, the specific activity changes around 100% even at elevated levels (at the maximum level of 8 mM/liter) of the nucleosides with pyrimidine bases (thymidine and deoxycytidine) constituting DNA (deoxyribonucleic acid). It is indicated that these nucleosides do not have the effect of inhibiting α-glucosidase.

COMPARATIVE EXAMPLE 2

In Comparative Example 2, examination has been made of the action of various nucleotides (5'-uridylic acid Na, 2'-uridylic acid Na, 5'-guanylic acid Na, 2'-guanylic acid Na, 5'-cytidylic acid Na, 2'-cytidylic acid Na, 5'-adenylic acid Na (AMP-Na), and adenosine diphosphate Na (ADP-Na)) on the porcine intestinal digestive enzyme α-glucosidase.

Using the same substrates and α-glucosidase as in the Example 1, experimental investigation has been made as to the presence or absence of the action of inhibiting the intestinal enzyme by the same method as in the Comparative Example 1. The results are shown in Table 2 hereinbelow. The enzyme activity is defined as 100% with no addition of any of the nucleotides, and specific activity (%) to the activity is shown at individual levels of each of the nucleotides.

In Table 2, the specific activity changes around 100% even at the increase (at the maximum level of 40 mM/liter) of the individual nucleotides (5'-uridylic acid Na, 2'-uridylic acid Na, 5'-guanylic acid Na, 2'-guanylic acid Na, 5'-cytidylic acid Na, 2'-cytidylic acid Na, 5'-adenylic acid Na (AMP-Na), and adenosine diphosphate Na (ADP-Na)). Thus, it is indicated that these nucleotides do not have an apparent effect of inhibiting α-glucosidase.

COMPARATIVE EXAMPLE 3

In Comparative Example 3, examination has been made of the action of various inosinic acids (5'-inosinic acid Na, 2'-inosinic acid Na, and 5'-inosinic acid K) as nucleic acid-series seasonings, on the porcine intestinal digestive enzyme α-glucosidase.

Using the same substrates and α-glucosidase as in the Example 1, experimental investigation has been made as to the presence or absence of the action of inhibiting the intestinal enzyme by the same method as in the Comparative Example 1. The results are shown in Table 3 hereinbelow. The enzyme activity is defined as 100% with no addition of any of the nucleic acid-series seasonings, and specific activity (%) to the activity is shown at individual levels of each of the nucleotides.

TABLE 2

| Name of substance | Specific activity to additive concentration | | | | |
|---|---|---|---|---|---|
| | 0 mMol/l | 10 mMol/l | 20 mMol/l | 30 mMol/l | 40 mMol/l |
| 5'-uridylic acid Na | 100.0 | 98.7 | 94.4 | 91.7 | 88.0 |
| 2'-uridylic acid Na *1 | 100.0 | 101.1 | 97.8 | 96.9 | 95.4 |
| 5'-guanylic acid Na | 100.0 | 97.1 | 92.7 | 92.1 | 89.8 |
| 2'-guanylic acid Na | 100.0 | 95.5 | 94.1 | 93.0 | 89.6 |
| 5'-cytidylic acid Na | 100.0 | 92.8 | 87.7 | 83.5 | 82.1 |
| 2'-cytidylic acid Na | 100.0 | 103.3 | 103.9 | 105.3 | 104.4 |
| 5'-adenylic acid Na (AMP-Na) | 100.0 | 99.3 | 99.5 | 92.6 | 94.3 |
| Adenosine diphosphate Na (ADP-Na) | 100.0 | 104.4 | 104.4 | 107.2 | 106.6 |

*1 Phosphoric acid is bonded at 2':2' or 3' position by ester bond.

TABLE 3

| Name of substance | Specific activity to additive concentration | | | | |
|---|---|---|---|---|---|
| | 0 mMol/l | 10 mMol/l | 20 mMol/l | 30 mMol/l | 40 mMol/l |
| 5'-inosinic acid Na | 100.0 | 97.4 | 95.6 | 94.4 | 89.0 |
| 2'-inosinic acid Na *1 | 100.0 | 97.1 | 93.9 | 92.6 | 88.1 |
| 5'-inosinic acid K | 100.0 | 96.3 | 90.1 | 84.4 | 82.4 |

*1 Phosphoric acid is bonded at 2':2' or 3' position by ester bond.

In Table 3, the specific activity changes around 100% to 80% even at elevated levels (at the maximum level of 40 mM/liter) of the individual inosinic acids as the individual nucleic acid-series seasonings (5'-inosinic acid Na, 2'-inosinic acid Na, and 5'-inosinic acid K). Thus, it is indicated that these inosinic acids do not have an apparent effect of inhibiting α-glucosidase.

EXAMPLE 5

The present Example 5 is an example wherein examination will be made about the actions of suppressing the increase in blood glucose level and suppressing insulin secretion after loading sugar.

Male Sugague-Dawley rats weighed 150 g were preliminarily fed with a standard diet of the composition shown below in Table 4, for 7 to 8 days. The feed and drinking water were fed ad libitum to the animals individually kept in a cage of an apartment type. The feeding room temperature was 22°±1° C. The feeding period was composed of two cycles of 12-hr light stage (7:00 to 19:00) and dark stage (19:00 to 7:00).

Prior to the experiment, the body weight was measured; animals with much difference in the body weight were excluded. Then, the animals were divided into groups each of 6 to 7 animals. The animals were starved overnight prior to the experiment.

Figure 5:
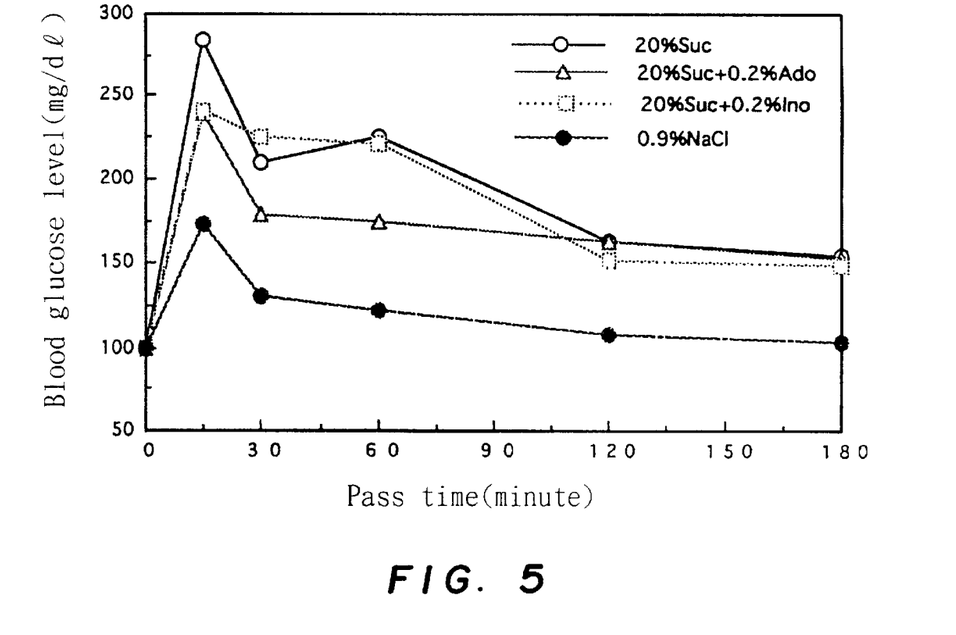
FIG. 5 depicts a graph of the action of a mixture of sucrose (Suc) and adenosine (Ado) or inosine (Ino) as a sugar material loaded onto rats, for suppressing the increase in blood glucose levels over time course.
Figure 6:
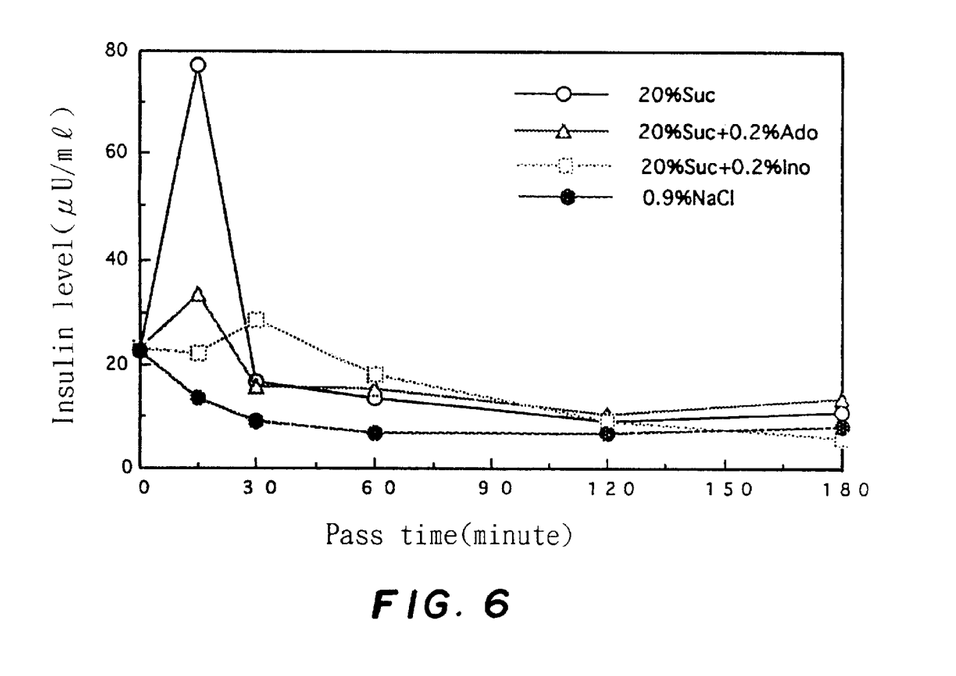
FIG. 6 depicts a graph of the action of a mixture of sucrose (Suc) and adenosine (Ado) or inosine (Ino) as a sugar material loaded onto rats, for suppressing the insulin levels over time course.

To each group of the rats were orally administered with sugar materials and the inhibitors (as the sugar solutions of the following composition) by means of stomach probes; arterial blood was sampled 0, 15, 30, 60, 120 and 180 minutes later to assay the blood glucose level (serum glucose level) and serum insulin level by the enzyme method. Composition of sugar solution:

A. 20% sucrose (control)
B. 20% sucrose+0.2% inosine
C. 20% sucrose+0.2% adenosine
D. physiological saline The dose was at a ratio of 250 mg sugar material (sucrose or starch)/100 g body weight; in the case of physiological saline, 2 ml was administered. FIG. 5 shows the graph depicting the change of blood glucose level over time course after the dosing; FIG. 6 shows the graph depicting the change of serum insulin level over time course. As apparently shown in these graphs, the blood glucose level and insulin level of the control group reached maximum 15 minutes after the dosing. Then, the levels were gradually lowered. This is consistent with various references previously reported. In FIG. 5, it is indicated that the sugar material (sucrose and the like) is finally degraded into glucose with the digestive enzyme α-glucosidase in small intestine, and glucose is then introduced into blood vessels in an enforced manner in 15 minutes, to promote rapidly the increase in blood glucose level. Such rapid increase in blood glucose level strongly promotes insulin secretion, and by the action of insulin, blood glucose level is gradually lowered, 15 minutes later and thereafter, eventually to the normal level.

Via a sucrose solution mixed with inosine or adenosine, the maximum blood glucose level 15 minutes later is apparently lower than the level in the control group given only sucrose. Significant difference is observed at a significant level of 1% between these blood glucose levels 15 minutes later. As shown in FIG. 6, furthermore, the insulin level is not rapidly elevated via the sucrose solution mixed with inosine or adenosine; 15 minutes later, the insulin level is lower than the level of the control group. Significant difference is observed at a significant level of 1% between the insulin levels 15 minutes later.

TABLE 4

| Standard diet of the composition | |
|---|---|
| Ingredient | (%) |
| Sucrose | 65.23 |
| Casein | 25.00 |
| Mixture of minerals AIN-76 | 3.50 |
| Mixture of vitamines AIN-76 | 1.00 |
| Choline tartrate | 0.27 |
| Corn oil | 5.00 |

EXAMPLE 6

The present Example 6 is an example wherein a base (cytosine) is used as the α-glucosidase inhibitor to examine the effect of suppressing the increase in blood glucose level and the effect of suppressing insulin secretion after the loading of sugar materials.

By the same method as in the Example 5, the effect of a sugar solution of sucrose mixed with cytosine on the suppression of the increase in the blood glucose level and the effect thereof on the suppression of the insulin secretion were examined 15 minutes after the administration. The results are shown in Table 5 below.

TABLE 5

| Composition of sugar solution administered | Blood glucose level mg/dl | Significant difference (Blood glucose level) | Insulin level µU/ml | Significant difference (Insulin level) |
|---|---|---|---|---|
| 20% Suc (control) | 284.5 | | 77.5 | |
| 20% Suc + 0.2% cytosine | 242.2 | ** | 28.3 | ** |

**0.01 > P

As apparently shown in Table 5, cytosine mixed with sucrose suppresses the increase in blood glucose level and insulin secretion significantly (at a significant level of 1%) 15 minutes later, compared with the control group. In conclusion, cytosine strongly inhibits the action of α-glucosidase.

EXAMPLE 7

The present Example 7 is an example wherein nucleic acid-series seasonings (inosinic acid K, adenylic acid Na, and guanylic acid Na) are used to examine the actions of suppressing the increase in blood glucose level and suppressing insulin secretion after the loading of sugar materials by the same method as in the Example 5.

The results are shown in Table 6 hereinbelow.

TABLE 6

| Composition of sugar solution administered | Blood glucose level mg/dl | Significant difference (Blood glucose level) | Insulin level µU/ml | Significant difference (Insulin level) |
|---|---|---|---|---|
| 20% Suc (control) | 284.5 | | 77.5 | |
| 20% Suc + 1% inosinic acid K | 199.0 | ** | 25.8 | ** |
| 20% Suc + 1% adenylic acid Na | 204.6 | ** | 26.7 | ** |
| 20% Suc + 1% guanylic acid Na | 217.9 | ** | 38.8 | * |

**0.01 > P
*0.05 > P

As apparently shown in Table 6, when inosinic acid K, adenylic acid Na, and guanylic acid Na in a mixture with sucrose were orally administered, the increase in blood glucose and the insulin secretion were significantly suppressed 15 minutes later.

In the Comparative Examples 2 and 3 regarding the inhibitory actions of the crude α-glucosidase enzyme from porcine intestine, the nucleotides (or inosinic acids) hardly exerted the inhibitory action (see Tables 2 and 3). Thus, it is assumed that the dosing of inosinic acids does not suppress the increase in blood glucose level or insulin secretion 15 minutes later, but the Example 7 brings about the outcome inconsistent to the assumption. As reported by Sonoda et at. (Biochimica et Biophysica Acta 521, pp. 55–66, (1978)), it has been known that the nucleotides (or inosinic acids) are enzymatically degraded after the intake through a process until they reach the intestine, so that the nucleotides are degraded into the corresponding nucleosides (a part thereof may be degraded into bases) for digestion and absorption. As shown in FIGS. 5 and 6, the nucleosides then generated by degradation inhibit α-glucosidase strongly, which may potentially cause the suppression of the increase in blood glucose level and insulin secretion.

EXAMPLE 8

Example 8 is an example wherein the actions of suppressing the increase in blood glucose level and suppressing insulin secretion are examined by using a sugar material, i.e., starch, mixed with individual α-glucosidase inhibitors (adenosine, cytosine, and inosine).

By the same method as in the Example 5, the action of suppressing the increase in blood glucose level and the action of suppressing insulin secretion were examined 15 minutes after the administration of sugar solutions of starch mixed with individual α-glucosidase inhibitors (adenosine, cytosine, and inosine). The results are shown in Table 7.

TABLE 7

| Composition of sugar solution administered | Blood glucose level mg/dl | Significant difference (Blood glucose level) | Insulin level µU/ml | Significant difference (Insulin level) |
|---|---|---|---|---|
| 15% Starch (control) | 289.5 | | 86.9 | |
| 15% Starch + 1.0% adenosine | 268.9 | — | 44.6 | — |
| 15% Starch + 1.0% cytosine | 255.0 | * | 47.7 | — |
| 15% Starch + 0.5% inosine | 269.2 | — | 68.7 | — |

*0.05 > P

As apparently shown in Table 7, it is indicated that 15 minutes after the oral administration of adenosine, cytosine or inosine mixed with starch, the increase in blood glucose level and the insulin secretion are both suppressed, compared with the control group.

EXAMPLE 9

Test of action of suppressing the increase in murine body weight:

Male Sugague-Dawley rats of age 4 weeks were preliminarily fed for 3 days with a standard diet of the composition shown below in Table 8. Subsequently, the animals were divided into 5 groups, each group being composed of 6 rats and with no difference in body weight. The feeding was carried out in an apartment-type cage per rat, with the feed and drinking water ad libitum. The feeding room temperature was 22°±1° C.; the feeding period was composed of 2 cycles of 12-hr light stage and dark stage (from 7:00 to 19:00, and from 19:00 to 7:00, respectively).

The feed given to the rats had the compositions shown below in Table 8; group A was fed with the standard diet containing sucrose as the sugar material; groups B and C were fed with test feed diets which were prepared by replacing 1% and 5%, respectively of the sucrose with adenosine; and groups D and E were fed with test feed diets which were prepared by replacing 1% and 5%, respectively of the sucrose with inosine. The body weight was measured 5 times at a one-week interval from the start of the test; at the termination of the test, blood collection and autopsy were carried out.

Test groups:

Group A: Sucrose (standard diet)

Group B: 1% adenosine addition group

Group C: 5% adenosine addition group

Group D: 1% inosine addition group

Group E: 5% inosine addition group

TABLE 8

| Ingredient | Group A Standard diet | Group B 1% adenosine diet | Group C 5% adenosine diet | Group D 1% inosine diet | Group E 5% inosine diet |
|---|---|---|---|---|---|
| Sucrose | 65.23 | 64.23 | 60.23 | 64.23 | 60.23 |
| Adenosine | — | 1.00 | 5.00 | — | — |
| Inosine | — | — | — | 1.00 | 5.00 |
| Casein | 25.00 | 25.00 | 25.00 | 25.00 | 25.00 |
| Mixture of minerals Ain-76 | 3.50 | 3.50 | 3.50 | 3.50 | 3.50 |
| Mixture of vitamines Ain-76 | 1.00 | 1.00 | 1.00 | 1.00 | 1.00 |
| Choline tartrate | 0.27 | 0.27 | 0.27 | 0.27 | 0.27 |
| Corn oil | 5.00 | 5.00 | 5.00 | 5.00 | 5.00 |

At the time of the initiation of the test, the tendency of slightly soft stool was observed in the 5% inosine addition group and 5% adenosine addition group. No abnormal finding was observed in the general health status and behavior of the experimental animals. No death case was observed. At the autopsy at the time of the termination of the test, no abnormal finding was observed in the organs.

Figure 7:
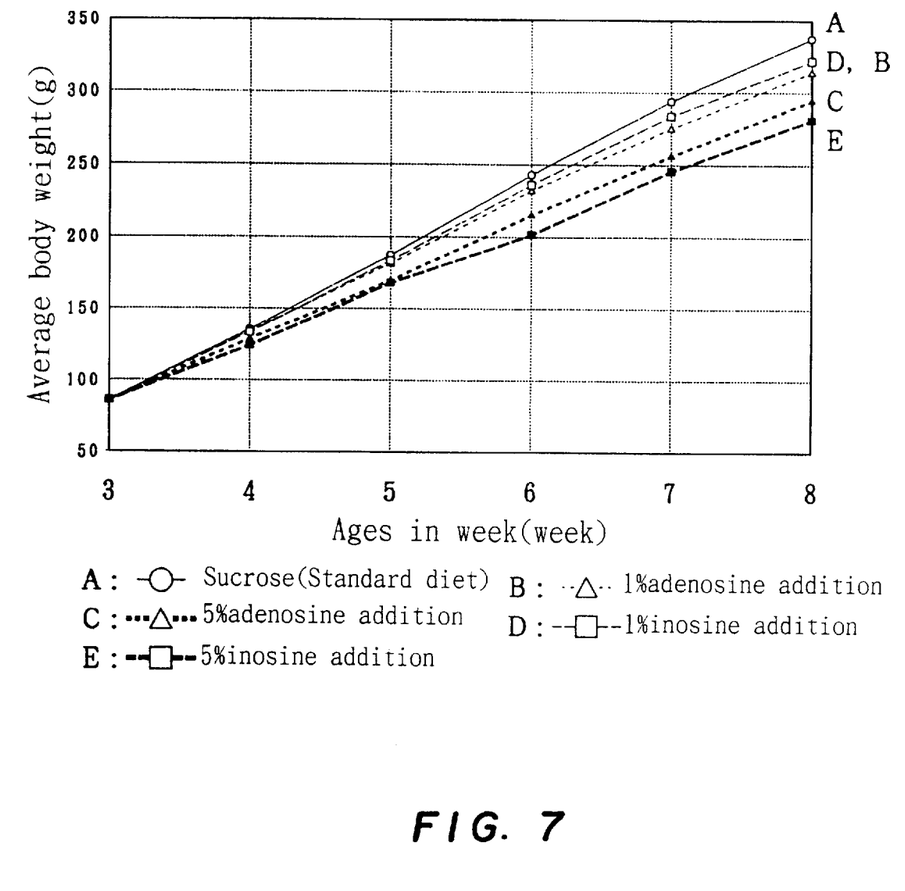
FIG. 7 depicts a graph of the mean body weight of rats loaded with a mixture of sucrose (Suc) and adenosine (Ado) or inosine (Ino) as a sugar material over time course.

The change of the body weight of the experimental animals is shown in FIG. 7; the increment of the body weight is shown in Table 9 hereinbelow.

TABLE 9

| | Body weight per age in week (g/rat) | | | | | | Gain of body weight through week age (g/rat) | |
|---|---|---|---|---|---|---|---|---|
| Test group | 3 ages in week | 4 ages in week | 5 ages in week | 6 ages in week | 7 ages in week | 8 ages in week | 3–5 ages in week | 5–8 ages in week |
| A group (Suc) | 86.2 | 135.3 | 187.3 | 242.7 | 294.1 | 337.5 | 101.1 | 150.2 |
| B group (1% adenosine) | 86.0 | 134.1 | 181.5 | 231.9 | 275.3 | 314.2 | 95.5 | 132.7 |
| C group (5% adenosine) | 86.0 | 128.5 | 169.8 | 215.3 | 256.8 | 295.0 | 83.8 | 125.2 |
| D group (1% inosine) | 86.0 | 133.3 | 183.3 | 236.1 | 283.8 | 321.8 | 97.3 | 138.5 |
| E group (5% inosine) | 85.9 | 124.0 | 167.8 | 201.6 | 245.6 | 281.3 | 81.9 | 113.5 |

As shown in Table 9 and FIG. 7, the increment of the body weight of the adenosine- or inosine addition group is less than that of the standard diet group after the 5-week feeding; the effect is more prominent as the increase of adenosine or inosine added. It is observed that the 5% adenosine addition (C) group and 5% inosine addition (E) group are significantly different from the standard diet group at significant levels of 5% and 1%, respectively.

EXAMPLE 10

Example in human subjects:

Healthy male adults (2), being not fat and remaining within +2SD, with no history of gastrointestinal disorders (intestinal resection etc.) or no history of diabetes mellitus, were assigned to Case I and Case II. For Case I, sucrose (50 g) as a control solution and a sugar solution of sucrose (50 g) mixed with adenosine (2.5 g) as a test solution were given; for Case II, sucrose (50 g) as a control solution and a sugar solution of sucrose (50 g) mixed with adenosine (1 g) as a test solution were given. Blood was intravenously sampled individually 0, 30, 60, 90 and 120 minutes later to assay the glucose level and insulin level. Herein, the volume each of the sugar solutions was 300 ml; the test was carried out in a double-blind fashion with not any information of the contents of the solutions given to the subjects and the test controller. Furthermore, the control solution and the test solutions were tested at an interval of 3 days. Still furthermore, adenosine was replaced with inosine, for carrying out the testing of Cases III and IV.

Figure 8:
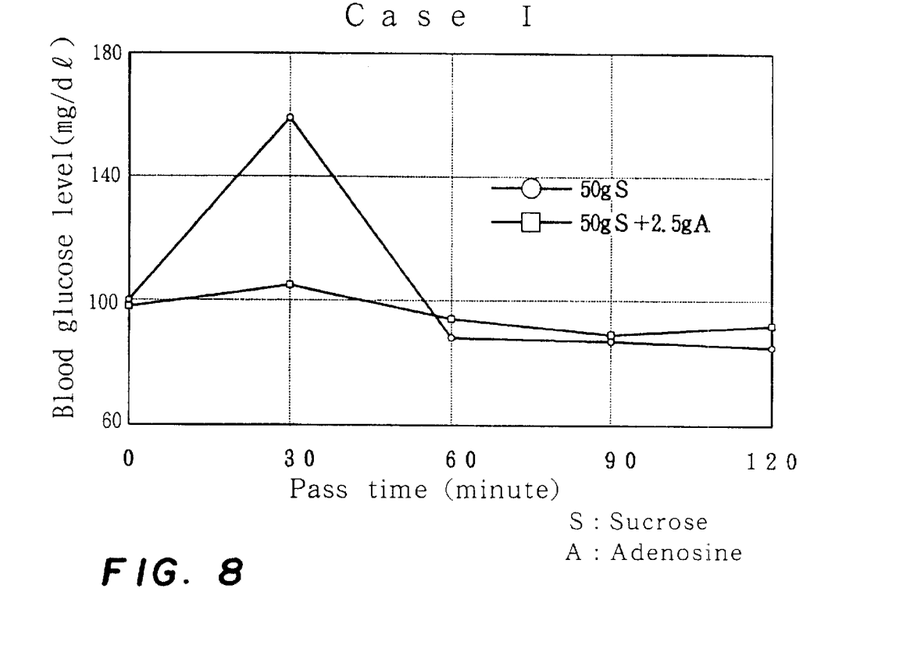
FIG. 8 depicts a graph of the change of the blood glucose level over time course in a human subject administered by oral with a sugar solution containing sucrose (50 g) and adenosine (2.5 g)
Figure 9:
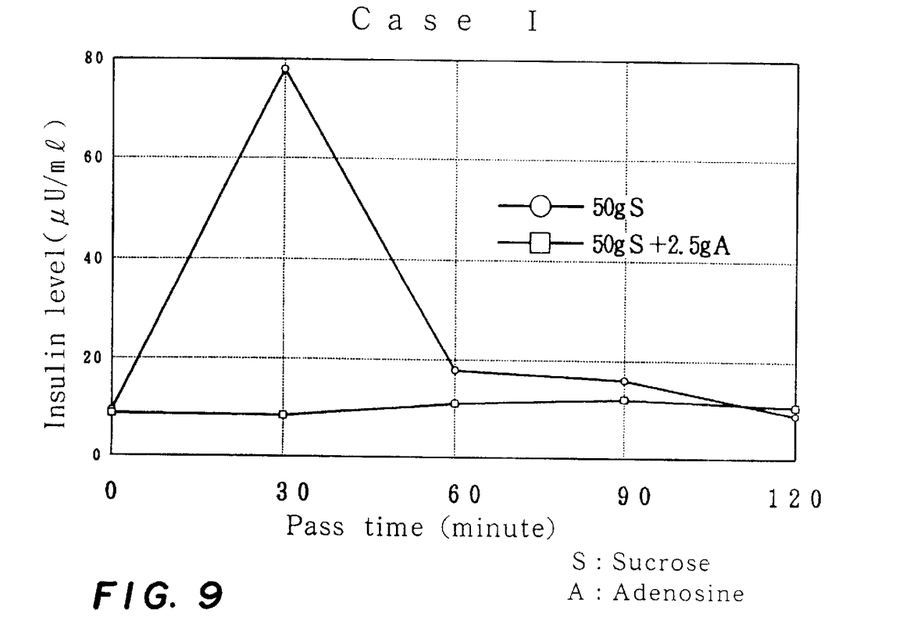
FIG. 9 depicts a graph of the change of the insulin level over time course in a human subject administered by oral with a sugar solution containing sucrose (50 g) and adenosine (2.5 g)
Figure 10:
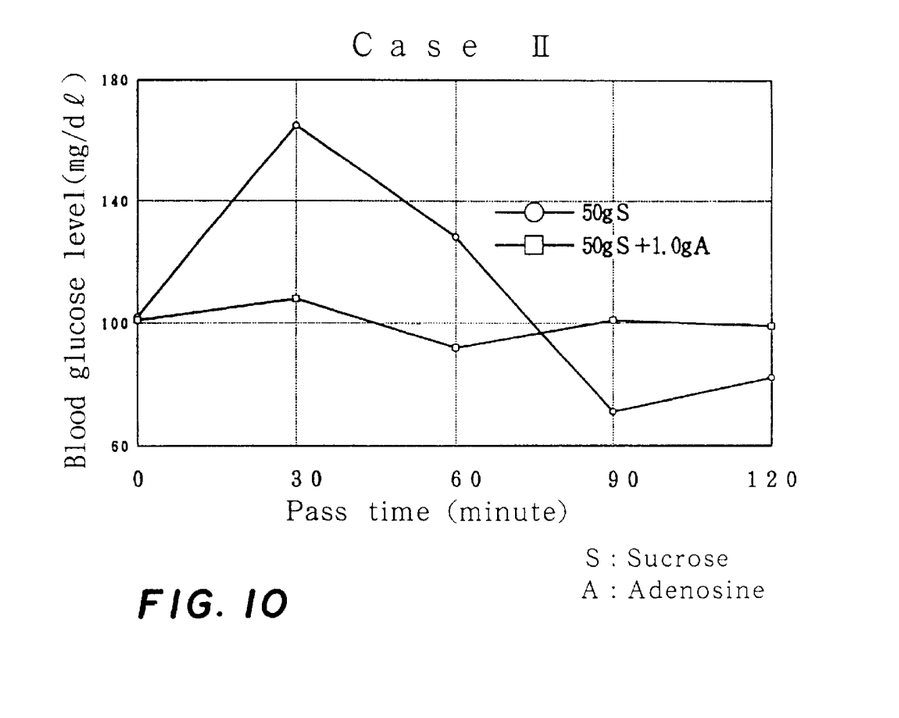
FIG. 10 depicts a graph of the change of the blood glucose level over time course in a human subject administered by oral with a sugar solution containing sucrose (50 g) and adenosine (1.0 g)
Figure 11:
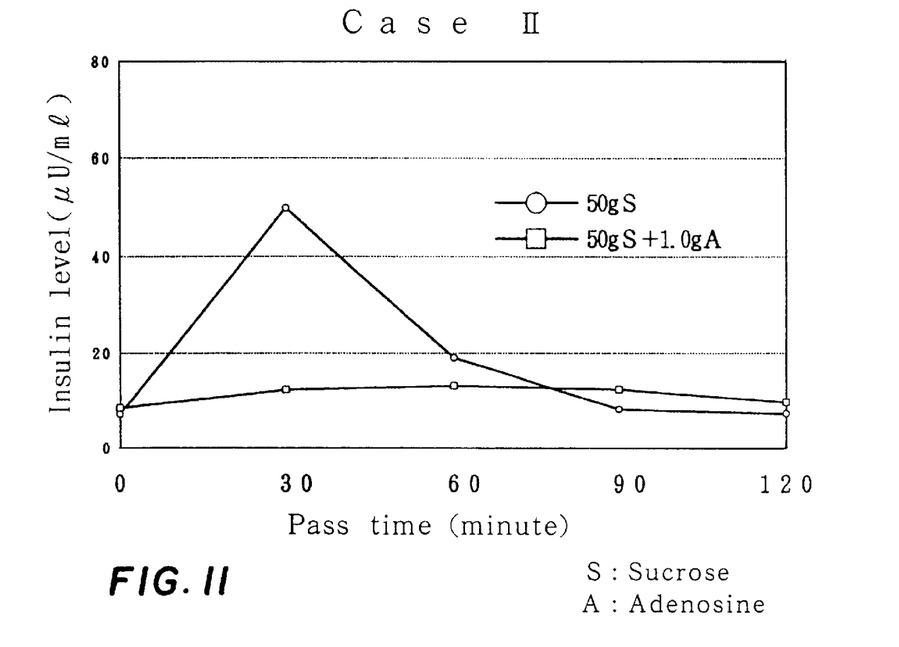
FIG. 11 depicts a graph of the change of the insulin level over time course in a human subject administered by oral with a sugar solution containing sucrose (50 g) and adenosine (1.0 g)
Figure 12:
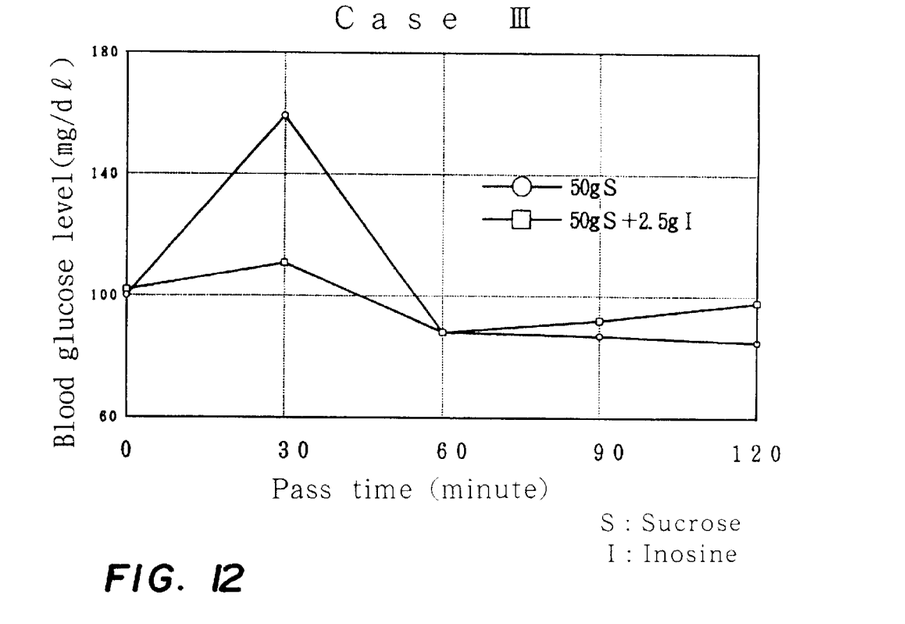
FIG. 12 depicts a graph of the change of the blood glucose level over time course in a human subject administered by oral with a sugar solution containing sucrose (50 g) and inosine (2.5 g)
Figure 13:
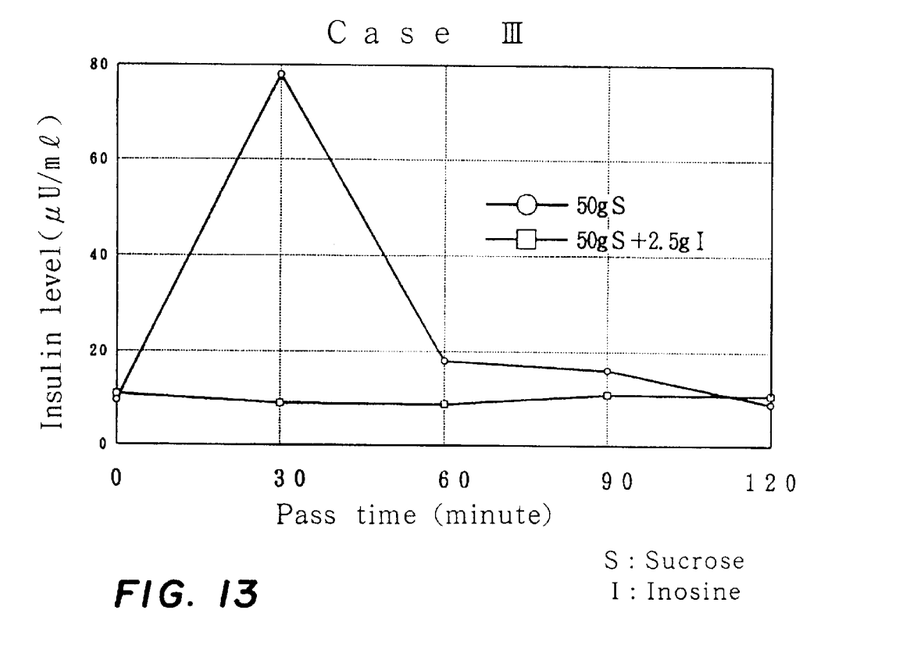
FIG. 13 depicts a graph of the change of the insulin level over time course in a human subject administered by oral with a sugar solution containing sucrose (50 g) and inosine (2.5 g)
Figure 14:
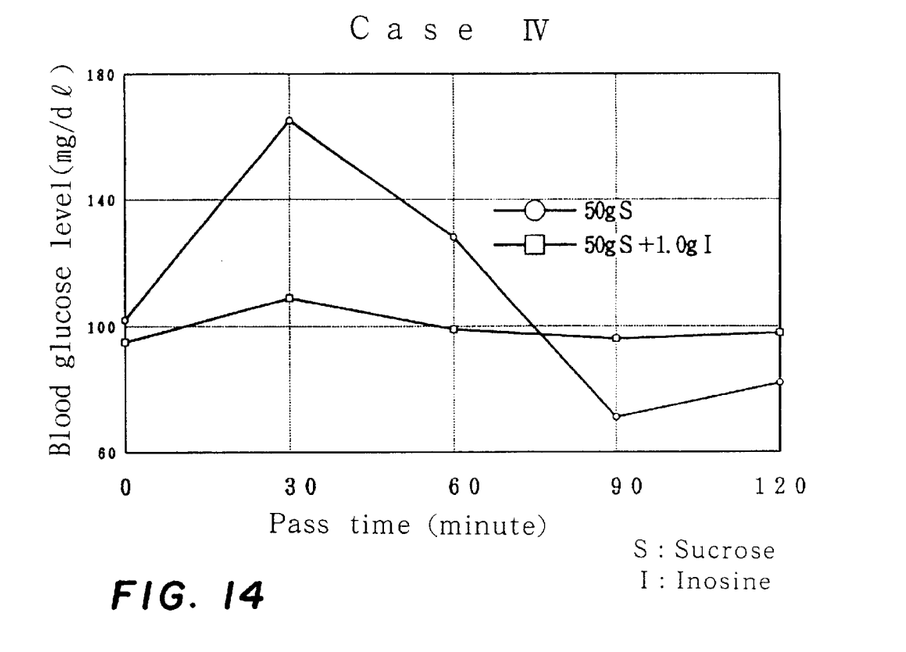
FIG. 14 depicts a graph of the change of the blood glucose level over time course in a human subject administered by oral with a sugar solution containing sucrose (50 g) and inosine (1.0 g)
Figure 15:
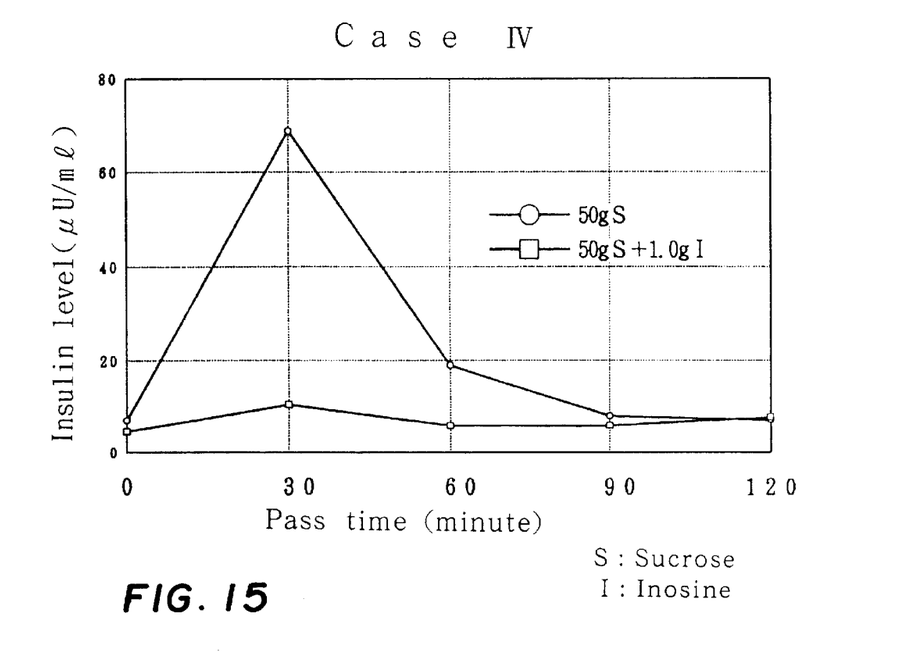
FIG. 15 depicts a graph of the change of the insulin level over time course in a human subject administered by oral with a sugar solution containing sucrose (50 g) and inosine (1.0 g).

The results are shown in graphs in FIGS. 8 to 15; for adenosine mixtures, FIGS. 8 and 9 show the change of blood glucose level and the change of insulin level, respectively of Case I; and FIGS. 10 and 11 show the change of blood glucose level and the change of insulin level, respectively of Case II. Similarly for inosine mixture, FIGS. 12 and 13 show the change of blood glucose level and the change of insulin level, respectively of Case III; and FIGS. 14 and 15 show the change of blood glucose level and the change of insulin level, respectively of Case IV. For any of the cases, FIGS. 8 to 15 indicate that the blood glucose level at maximum 30 minutes after the administration is apparently lower for the test solutions than the level for the control solutions, and that the insulin level is not elevated. During the testing period, no complaint such as abdominalgia, diarrhea or abdominal inflammation has been claimed from any of the subjects.

EXAMPLE 11

Example of the use of the α-glucosidase inhibitor as the sweetener in coffee:

Within such a range that the effect of suppressing α-glucosidase can be exerted, 1 part by weight of adenosine and 5 parts by weight of inosine were mixed to 100 parts by weight of sucrose for the preparation of a sweetener. A sample prepared by dissolving sucrose alone at 10% was designated as a control, while a sample prepared by dissolving the sweetener at the same amount was designated as a test sample.

Ten skilled panelists (10) tasted individual coffee solutions for the functional testing of the flavor and taste. Consequently, 2 of the 10 panelists felt the coffee with addition of 5% adenosine mildly bitter and rough; and 1 of them felt the taste unpleasant. One of the ten panelists felt the coffee with addition of 5% inosine +1% adenosine mildly bitter; 3 of the 10 panelists felt the coffee with addition of 1% inosine +1% adenosine preferably rough; others made an answer of no difference among the samples. Based on the outcome, it is indicated that the α-glucosidase inhibitor of the present invention can be used as a sweetener for drinks.

EXAMPLE 12

Example of the use of the sweetener of the present invention as a sweet material to prepare a butter roll:

Using the same sweetener as in the Example 11, a butter roll was prepared, prior to the functional test to be carried out. Using sucrose as a control sweetener, a butter roll was similarly prepared. The material composition of the butter roll using the control sucrose is as follows; flour (500 g), edible salt (5 g), milk (300 ml), egg yolk (20 g), sucrose (40 g), and fresh yeast (25 g). The control butter roll was prepared by the routine process. At the preliminary fermentation, then, the increment of the sample to the control was about 10% at the volume ratio.

A subjective sweetener was prepared at a final ratio of about 10 parts by weight (6 g) of inosine or adenosine to 100 parts by weight of carbohydrate, while starch and sucrose were used in the control. The material composition of the butter roll was the same except for the substitution of the control sucrose with the sweetener. Consequently, 3 of the 10 panelists made an answer that its crisp and hard feeling was preferable, but no one made an answer that tasty difference was evident.

EXAMPLE 13

Example of the use of the sweetener of the present invention as the sweet material for the preparation of sweet chocolate:

Using the same sweetener as in the Example 11, sweet chocolate was prepared prior to the functional test. Using sucrose alone as the control sweetener, sweet chocolate was prepared in the same manner. Bitter chocolate block (100 g) was pulverized, followed by addition of the sweetener or sucrose prior to solubilization and solidification. The functional test of the prepared sweet chocolates was carried out by the same method as in the Examples 11 and 12, but no specific difference in the taste, especially in bitterness, was observed.

EXAMPLE 14

Example of the use of the sweetener of the present invention as the sweet material for the preparation of hard candy:

Distilled water (87 g) was added to sucrose (220 g) prior to heating to 177° C. for 30 minutes. Then, keeping the temperature at 100° C., inosine or adenosine (5 g) was added in three portions for sufficient stirring. Subsequently, the mixture was poured into a mold preliminarily prepared, which was left to stand for cooling. As a control, hard candy was prepared by the same method, except for no addition of inosine or adenosine. Consequently, hard candy (249 g) with about 2% of inosine or adenosine was generated. The taste and flavor of the hard candy was absolutely the same as those of hard candies prepared by the same method except for no inclusion of inosine or adenosine therein.

Industrial Applicability

When used in combination with one or two or more digestible sugars selected from sucrose, starch and starch-derived oligosaccharide, the constituent of the α-glucosidase inhibitor, namely the nucleotide, nucleoside or base as the structural component of nucleic acid, mildly suppresses the action of the digestive enzyme in small intestine, namely, α-glucosidase to suppress rapid increase in blood glucose level and then suppress insulin secretion at a lower level.

The inhibiting action of the α-glucosidase inhibitor of the present invention is so mild that a large amount of the α-glucosidase inhibitor at a ratio of 0.5 to 30 parts by weight to 100 parts by weight of the total carbohydrate (total sugar material) intake can be blended and used. Thus, the α-glucosidase inhibitor can be used as a food material or a sweetener to be added and mixed into a food.

The food and the sweetener, containing the α-glucosidase inhibitor of the present invention, are useful for healthy persons for the prophylaxis of adult diseases such as obesity and diabetes mellitus; for fat persons and patients with diabetes mellitus, a wide range of foods and sweeteners suitable for dietary treatment can be provided, which can relieve the regulation of the intake of sugars such as sucrose, starch, and starch-derived oligosaccharide.

The foods containing the α-glucosidase inhibitor of the present invention mildly inhibit the action of α-glucosidase, thereby suppressing rapid increase in blood glucose level and also suppressing insulin secretion at a lower level. Thus, it is observed that the intake thereof for a long term has an effect of realizing a slim body.

The feeds containing the α-glucosidase inhibitor of the present invention relieve the tendency of obesity, so that the feeds are useful as feeds for preventing the occurrence of obesity and diabetes mellitus in pets; the feeds are also useful as feeds for animals for meat with less fat.

What is claimed is:

1. An α-glucosidase inhibitor composition containing, as an effective ingredient, at least one substance selected from the group consisting of nucleotides, nucleosides and nucleic acid-derived bases, and having a mild action inhibiting α-glucosidase.

2. An α-glucosidase inhibitor according to claim 1, wherein the effective ingredient is a nucleotide selected from the group consisting of adenylic acid, guanylic acid, cytidylic acid, uridylic acid, inosinic acid and salts thereof.

3. An α-glucosidase inhibitor according to claim 1, wherein the effective ingredient is a nucleoside selected from the group consisting of guanosine, deoxyguanosine, adenosine, deoxyadenosine, cytidine, uridine, inosine and deoxyinosine.

4. An α-glucosidase inhibitor according to claim 1, wherein the effective ingredient is a nucleic acid-derived base selected from the group consisting of cytosine and adenine hydrochloride salts.

5. A composition consisting essentially of an α-glucosidase inhibitor selected from the group consisting of nucleotides, nucleosides and nucleic acid-derived bases and at least one digestible sugar selected from the group consisting of sucrose, starch and starch-derived oligosaccharide, said inhibitor having a mild digestive action on sugar and activity in suppressing insulin secretion.

6. A composition according to claim 5, wherein the α-glucosidase inhibitor is 0.5 to 30 weight percent of the composition.

7. A food containing, as an additive, the composition according to claim 5.

8. A health food containing, as an additive, 0.5 to 30 parts by weight of the α-glucosidase inhibitor according to claim 1 per 100 parts by weight total carbohydrate (sugar material) in the food.

9. A composition according to claim 5 wherein said inhibitor is a nucleotide.

10. A composition according to claim 9, wherein said nucleotide is selected from the group consisting of adenylic acid, guanylic acid, cytidylic acid, uridylic acid, inosinic acid and salts thereof.

11. A composition according to claim 5 wherein said inhibitor is a nucleoside.

12. A composition according to claim 11 wherein said nucleoside is selected from the group consisting of guanosine, deoxyguanosine, adenosine, deoxyadenosine, cytidine, uridine, inosine and deoxyinosine.

13. A composition according to claim 5 wherein said inhibitor is a nucleic acid-derived base.

14. A composition according to claim 5 wherein said nucleic acid-derived base is the hydrochloride salt of cytosine or adenine.

15. A method of treating diabetes mellitus in a patient comprising administering to said patient an α-glucosidase inhibitor selected from the group consisting of nucleotides, nucleosides and nucleic acid-derived bases.

16. A method of reducing weight of a patient comprising administering to said patient a food containing an α-glucosidase inhibitor selected from the group consisting of nucleotides, nucleosides and nucleic acid-derived bases.

* * * * *